(12) United States Patent
Terstappen et al.

(10) Patent No.: US 6,287,791 B1
(45) Date of Patent: Sep. 11, 2001

(54) MULTIDIMENSIONAL CELL DIFFERENTIAL ANALYSIS

(75) Inventors: Leon W M M Terstappen, Palo Alto; Chia-Huei Chen, San Jose, both of CA (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 08/239,265

(22) Filed: May 6, 1994

Related U.S. Application Data

(63) Continuation of application No. 07/823,911, filed on Jan. 22, 1992, now abandoned.

(51) Int. Cl.[7] .................................................. G01N 33/543
(52) U.S. Cl. .................. 435/7.24; 435/7.25; 435/808; 435/968; 435/526; 435/172; 435/518; 435/800; 435/805
(58) Field of Search ................................. 435/7.24, 7.25, 435/808, 968; 436/526, 172, 800, 805

(56) References Cited

U.S. PATENT DOCUMENTS

| | | | |
|---|---|---|---|
| 4,284,412 | 8/1981 | Hansen et al. | 23/230 |
| 4,520,110 | 5/1985 | Stryer et al. | 436/501 |
| 4,542,104 | 9/1985 | Stryer et al. | 436/536 |
| 4,727,020 | 2/1988 | Recktenwald | 435/6 |
| 4,845,653 | 7/1989 | Conrad et al. | 364/521 |
| 4,876,190 | 10/1989 | Recktenwald | 435/7 |
| 4,957,870 | * 9/1990 | Lee et al. | 436/63 |
| 5,047,321 | 9/1991 | Loken et al. | 435/6 |

OTHER PUBLICATIONS

Davis et al "Clinical Flow Cytometric Reticulocyte Analysis" Pathobiology 58:99–106 1990.*
Dako Bulletin "The CD System" 1989.*
Basch, R.S. et al "Expression CD4 by Human Megakaryocytes" Proc. Natl. Acad. Sci:87 p. 8085–9 1990.*
Kansas, G.S. et al "Expression of the CD11/CD18, Leukocyte Adhesion Molecule 1, and CD44 Adhesion Molecules During Normal Myeloid and Erythroid Differentiation in Humans" Blood vol. 76(12) p. 2483–92 1990.*

* cited by examiner

Primary Examiner—Bao-Thuy L. Nguyen
(74) Attorney, Agent, or Firm—David W. Highet

(57) ABSTRACT

This invention relates to an improved method for the multiparameter analysis of cells from peripheral blood or bone marrow. The method uses a nucleic acid dye, at least two fluorescently labelled monoclonal antibodies and at least two light scatter parameters to differentiate and discriminate between and among different cells in the blood or bone marrow.

15 Claims, 4 Drawing Sheets

(4 of 4 Drawing Sheet(s) Filed in Color)

MULTIDIMENSIONAL CELL DIFFERENTIAL ANALYSIS

This application is a continuation, of application Ser. No. 07/823,911, filed Jan. 22, 1992 now abandoned.

FIELD OF THE INVENTION

This invention relates to the field of flow cytometry and more particularly to the analysis of hematopoietic cells from blood and bone marrow. The invention enables the calculation of blood and bone marrow differentials by multi-parameter flow cytometry.

BACKGROUND OF THE INVENTION

In U.S. Pat. No. 5,047,321, Loken and Terstappen described the multi-parameter analysis of cellular components in a body fluid. The body fluids described included blood and bone marrow. Using a combination of two nucleic acid dyes, a fluorescently labelled monoclonal antibody and two light scatter parameters, Loken and Terstappen were able to discriminate between and among various components of blood and bone marrow, count the number of cells within each component and provide a differential analysis of each.

Loken and Terstappen used LDS-751 (Exciton) as a DNA dye, Thiazole Orange ("TO", Molecular Probes, Inc.) as an RNA dye, a fluorescently labelled anti-CD45 monoclonal antibody and forward and orthogonal light scatter on whole blood or bone marrow aspirates. Using these five parameters, they were able to detect and differentiate between erythrocytes, reticulocytes, nucleated erythrocytes, platelets, lymphocytes, monocytes, neutrophilic granulocytes, basophilic granulocytes, eosinophilic granulocytes and precursors of all nucleated cells.

Specifically, erythrocytes were characterized by light scatter and lack of fluorescence. Reticulocytes were characterized similar to erythrocytes by light scatter but could be discriminated from erythrocytes based upon their staining with Thiazole Orange. Platelets were characterized by their low light scatter and staining with LDS-751. Leukocytes were characterized by their large light scatter, LDS-751 and Thiazole Orange fluorescence and anti-CD45 fluorescence. Among the leukocytes, lymphocytes were characterized by high fluorescence intensity of anti-CD45 staining; monocytes had similar antibody fluorescence intensity with larger light scatter; neutrophilic granulocytes had dimmer antibody fluorescence intensity with large light scatter; and eosinophilic granulocytes had an antibody fluorescence intensity similar to monocytes but had a larger orthogonal light scatter and lower forward light scatter than monocytes.

While the method has utility for most analyses, a limitation in this method exists. The combination of LDS-751 with Thiazole Orange and anti-CD45 fluorescence does not permit full discrimination among the erythroid lineage (i.e., it does not permit identification of orthochromatic normoblasts, normoblasts and erythroblasts and does not permit differentiation between mature and immature reticulocytes) and does not permit the identification of proliferating myeloid cells and non-hematopoietic cells (i.e., stromal and epithelial cells).

Taking these limitations into account, there is a need for an improved method for the identification of and discrimination among the cellular components of blood and bone marrow.

SUMMARY OF THE INVENTION

The present invention comprises a method for the simultaneous, multi-parameter analysis of cells in a body fluid, such as blood and bone marrow. For each cell in a sample of cells taken from blood or bone marrow, at least two measures of light scatter are taken and at least three measures of fluorescence are taken. The three fluorescence components comprise one nucleic acid dye having a preference for RNA, a first fluorescently labelled cell surface marker which recognizes an antigen expressed in differential amounts on cells of different lineages in the hematopoietic system, and a second fluorescently labelled cell surface marker which recognizes erythrocyte precursors and proliferating cells. The fluorescence emission of the three stains must be distinguishable.

In this method, the cells are mixed separately or together with the nucleic acid dye and cell surface markers. The stained cells then are analyzed by means of flow cytometry wherein the cells are passed substantially one at a time through one or more sensing regions (wherein each of the cells is exposed separately individually to a source of light at a single wavelength and measurements of at least two light scatter parameters and measurements of at least three fluorescence emissions are separately recorded for each cell), and the data recorded for each cell is analyzed in real time or stored in a data storage and analysis means, such as a computer. U.S. Pat. No. 4,284,412 describes the configuration and use of a typical flow cytometer equipped with a single light source while U.S. Pat. No. 4,727,020 describes the configuration and use of a flow cytometer equipped with two light sources.

In a preferred embodiment of this invention, the cell surface markers comprise monoclonal antibodies. The first cell surface marker is an anti-CD45 monoclonal antibody, such as anti-HLe-1 (Becton Dickinson Immunocytometry Systems, "BDIS"). The second cell surface marker comprises one or more monoclonal antibodies that recognize proliferating cells and erythrocyte precursors. In the preferred embodiment, the antibody is an anti-CD71 monoclonal antibody such as anti-Transferrin Receptor (BDIS).

In another embodiment, a third cell surface marker can be selected from the group consisting of anti-CD61, anti-CD41 or anti-CD42, and pan platelet monoclonal antibodies. The addition of a pan platelet antibody aids in the separation of platelets and can aid in the identification of platelet precursors (i.e., megakaryocytes).

Each of these antibodies referred to herein has been given a "cluster designation" number (or "CD" number) by the International Workshop and Conference on Human Leukocyte Differentiation Antigens and many examples of each antibody have been made commercially as well as independently and submitted to the Workshop for clustering.

The antibodies can be directly conjugated to a fluorescent label or can be indirectly labelled with, for example, a goat anti-mouse antibody conjugated directly to the fluorescent label. Direct conjugation is preferred, however. Fluorescent labels which can be used in the practice of this invention include phycoerythrin ("PE"), fluorescein isothiocyanate ("FITC"), allophycocyanin ("APC"), Texas Red ("TR", Molecular Probes, Inc.), peridinin chlorophyll complex ("PerCp"), CY5 (Biological Detection System) and conjugates thereof coupled to PE (e.g., PE/CY5, PE/APC and PE/TR). A preferred combination of labels is PE and PE/CY5. Thiazole Orange is the preferred nucleic acid dye. U.S. Pat. No. 4,520,110 describes the composition and use of PE conjugated to a monoclonal antibody, and U.S. Pat. No. 4,542,104 describes the composition and use of PE in a paired conjugate format. U.S. Pat. No. 4,876,190 describes the composition and use of PerCp.

In a preferred method, a sample of blood or bone marrow is taken and is mixed with an RNA dye, a fluorescently labelled anti-CD45 monoclonal antibody and a fluorescently labelled anti-CD71 monoclonal antibody. After mixing, the sample is run on a flow cytometer, such as a FACScan™ brand flow cytometer (BDIS) equipped with a laser light source. Cells are analyzed substantially one at a time and orthogonal light scatter, forward light scatter and three fluorescence emissions are separately recorded for each cell. The five parameters recorded for each cell are then used in one or more combinations to identify and characterize each cell.

The method of this invention can be used to both identify and discriminate between cell populations and stages of development as well as to enumerate the numbers of cells in each population and stage.

BRIEF DESCRIPTION OF THE DRAWINGS

The file of this patent contains at least one drawing drawing executed in color. Copies of this patent with color drawing(s) will be provided by the Patent and Trademark Office upon request and payment of the necessary fee.

DETAILED DESCRIPTION OF THE INVENTION

Normal whole blood or normal bone marrow aspirates were obtained from healthy volunteers as described in U.S. Pat. No. 5,047,321. Fetal bone marrows were obtained from aborted fetuses 17–25 weeks of gestational age. Bone marrow cells were isolated by flushing intramedullary cavities of the femurs with RPMI 1640 (Gibco) with 10% fetal calf serum ("FCS") followed by $NH_4Cl$ lysis.

For each test, 10 µl of whole blood or bone marrow was used. To each test were added, 10 µl of TO (1 µg/ml in a solution of phosphate buffered saline ("PBS"), 0.5% bovine serum albumin ("BSA") and 0.1% $NaN_3$), 0.25 µg/test of anti-CD71 PE (in a solution of PBS, 0.5% BSA and 0.1% $NaN_3$), and 0.25 µg/test of anti-CD45 PE/CY5 (in a solution of PBS, 0.5% BSA and 0.1% $NaN_3$). The reagents were incubated with the body fluid for approximately 15 minutes at room temperature and in the dark. 1 ml of a 0.5% solution of paraformaldehyde in PBS then was added. The samples then were run on a FACScan brand flow cytometer equipped with an argon laser at 488 nm. Data was recorded and analyzed on an HP310 computer equipped with LYSIS II™ software (BDIS) and Paint-a-Gate™ software (BDIS). (Paint-a-Gate™ software and method of use are further described in U.S. Pat. No. 4,845,653.)

Figure 1A:
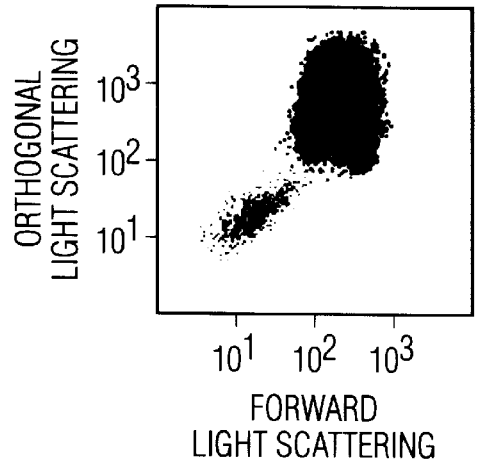
FIG. 1 comprises a series of six dot plots of peripheral whole blood cells which had been labelled with TO, anti-CD45 PE/CY5 and anti-CD71 PE, wherein (A) is a plot of orthogonal light scatter versus forward light scatter, (B) is a plot of log TO fluorescence versus log PE/CY5 fluorescence, (C) is a plot of orthogonal light scatter versus log PE/CY5 fluorescence, (D) is a plot of log PE fluorescence versus log TO fluorescence, (E) is a plot of log PE fluorescence versus log PE/CY5 fluorescence, and (F) is a plot of forward light scatter versus log PE/CY5 fluorescence.
Figure 1D:
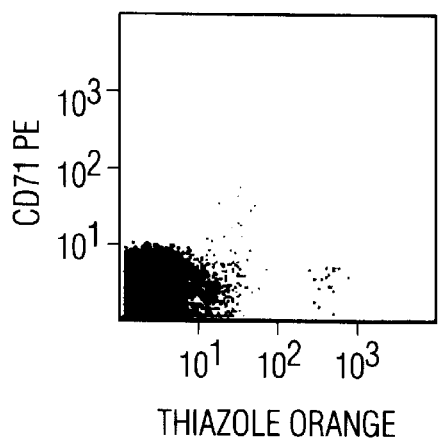
Figure 1B:
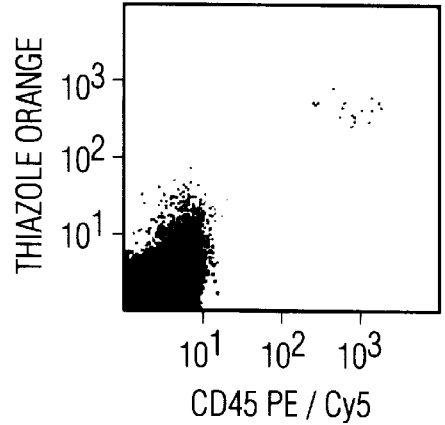
Figure 1E:
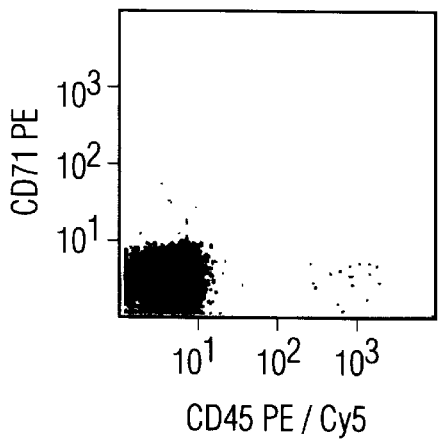
Figure 1C:
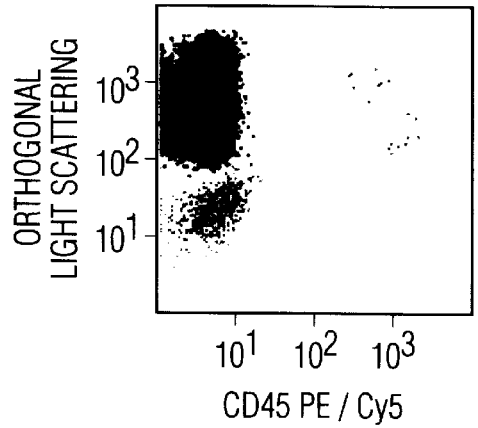
Figure 1F:
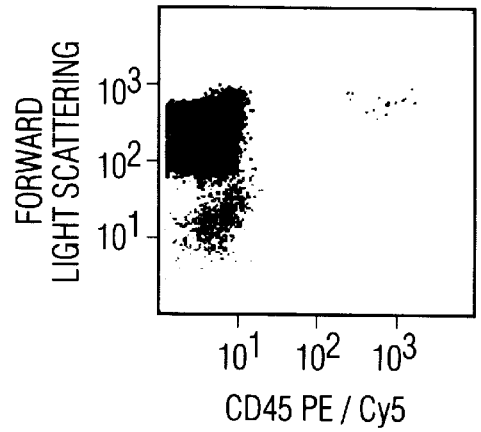
Figure 2A:
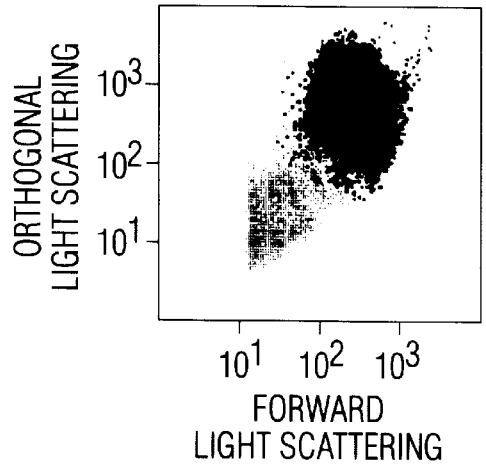
FIG. 2 comprises a series of six dot plots of fetal bone marrow cells which had been labelled with TO, anti-CD45 PE/CY5, anti-CD71 PE, wherein (A)–(F) have the axes as in FIG. 1.
Figure 2D:
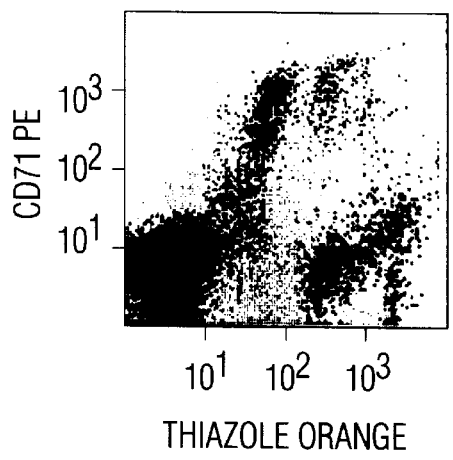
Figure 2B:
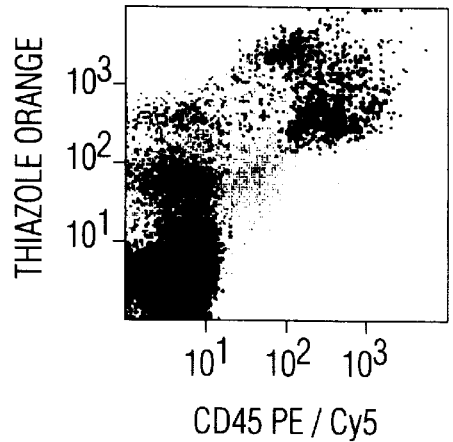
Figure 2E:
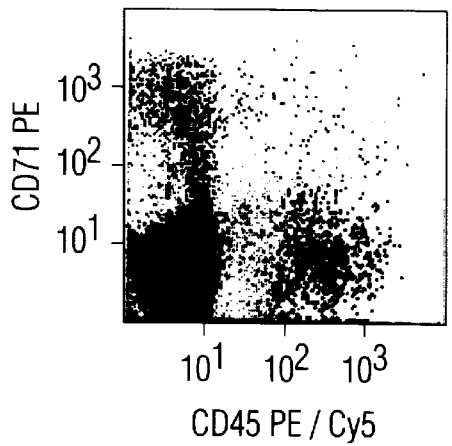
Figure 2C:
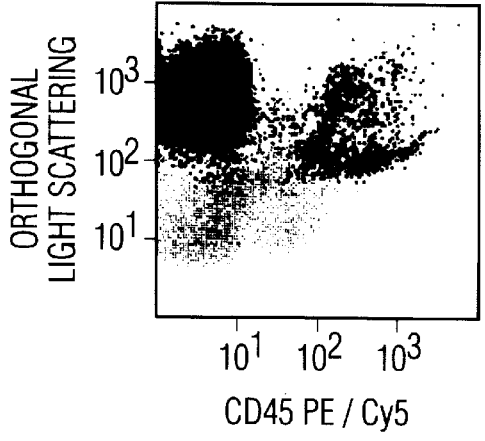
Figure 2F:
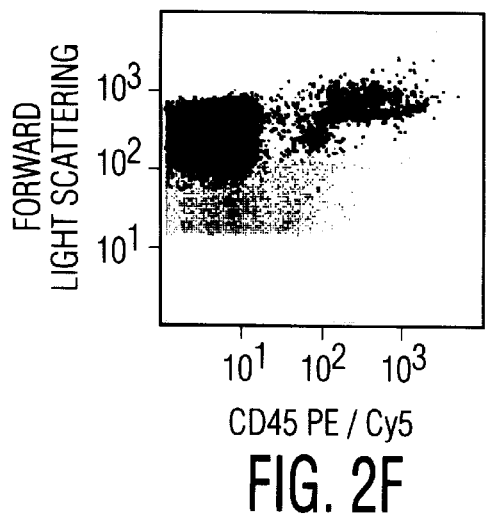

Referring to FIG. 1, six dot plots (or scattergrams) are shown for a normal peripheral whole blood sample. Erythrocytes are depicted as red, platelets as light blue, reticulocytes as yellow, immature reticulocytes as violet and leukocytes as green. In FIG. 2, six dot plots are shown for a normal fetal bone marrow sample. The color scheme is the same as in FIG. 1, however, nucleated erythrocytes are depicted as light blue, platlets as gray and proliferating cells as black.

Figure 3A:
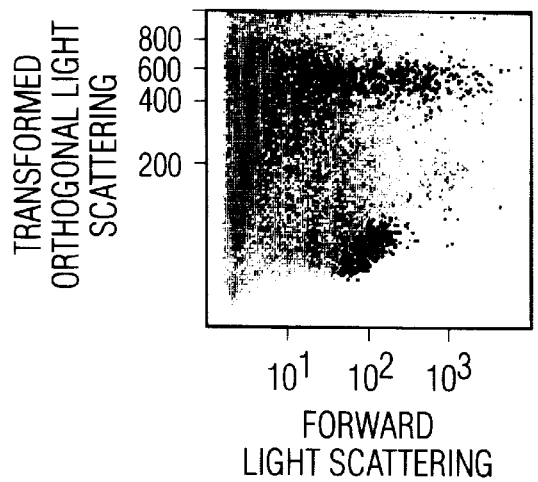
FIGS. 3 and 4 comprises a series of six dot plots of peripheral whole blood cells from FIGS. 1 and 2 respectively with a threshold set for TO fluorescence, wherein (A) is a plot of transformed orthogonal light scatter versus forward light scatter, (B) is a plot of log TO fluorescence versus log PE/CY5 fluorescence, (C) is a plot of transformed orthogonal light scatter versus log PE/CY5 fluorescence, (D) is a plot of log PE fluorescence versus log TO fluorescence, (E) is a plot of log PE fluorescence versus log PEICY5 fluorescence, and (F) is a plot of forward light scatter versus log PE/CY5 fluorescence.
Figure 3D:
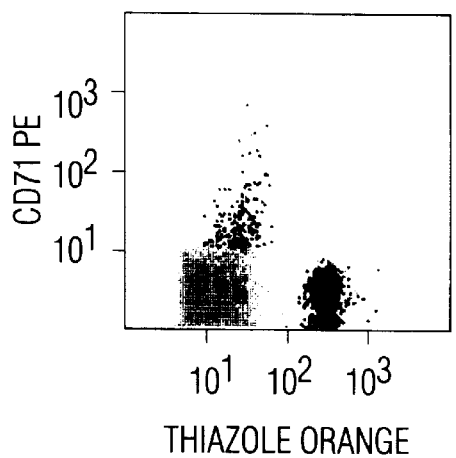
Figure 3B:
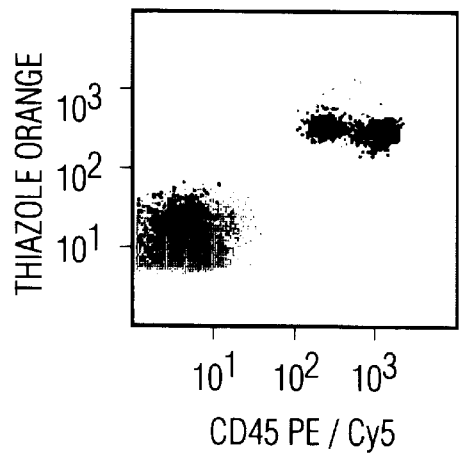
Figure 3E:
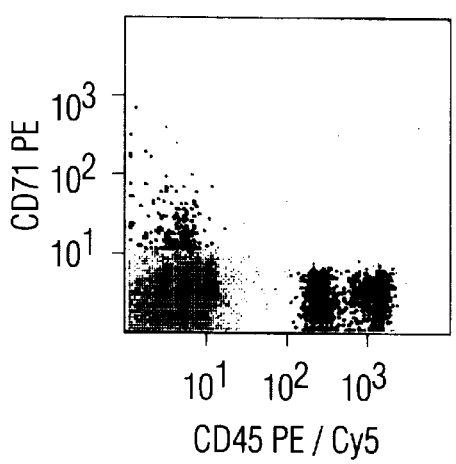
Figure 3C:
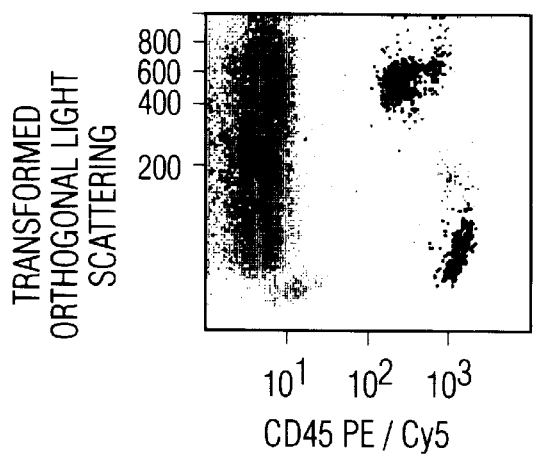
Figure 3F:
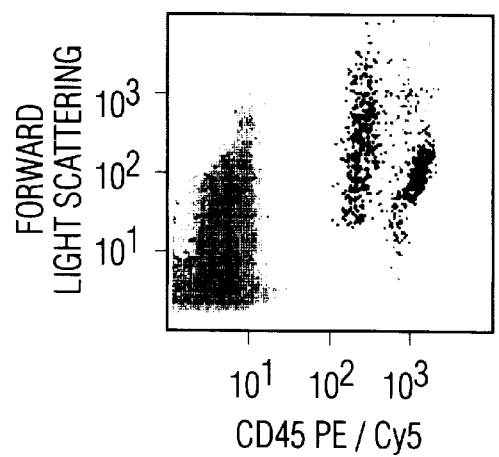
Figure 4A:
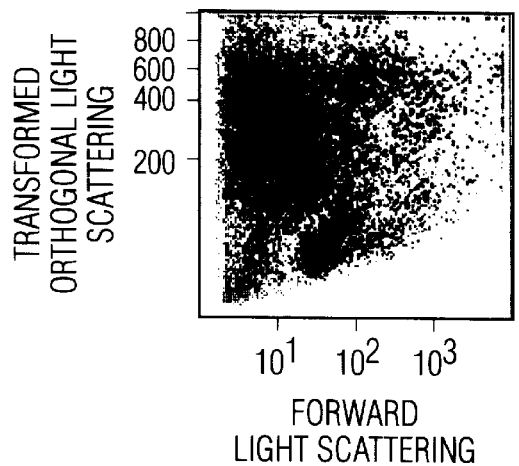
Figure 4D:
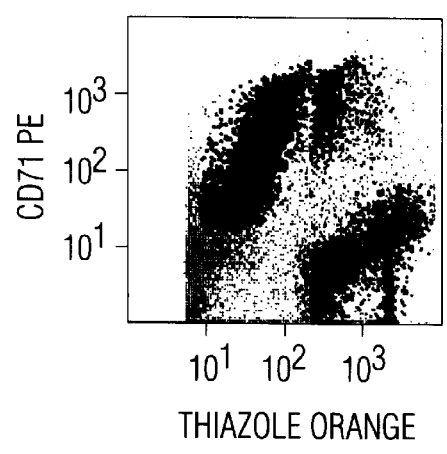
Figure 4B:
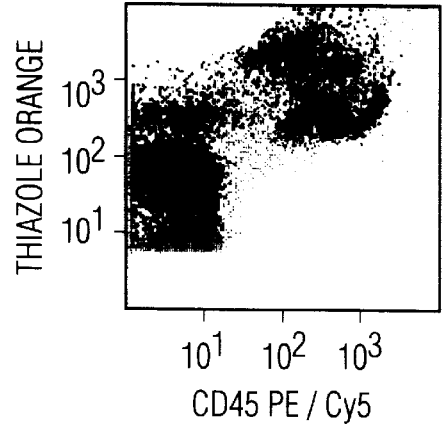
Figure 4E:
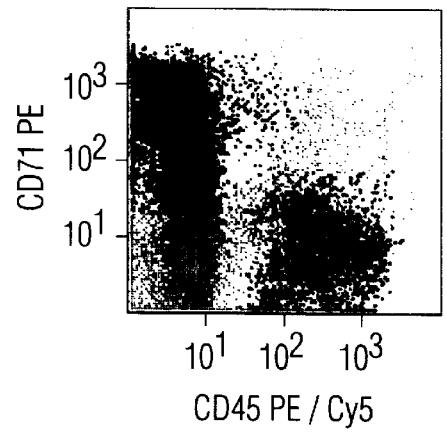
Figure 4C:
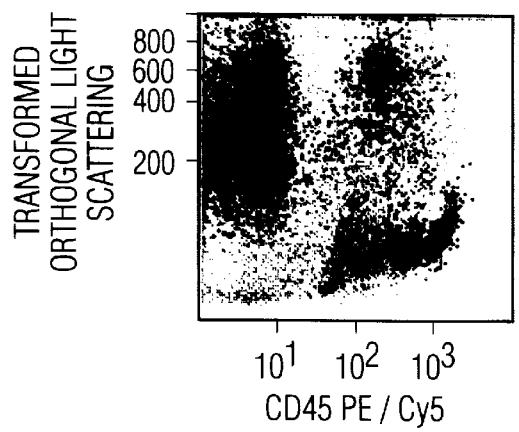
Figure 4F:
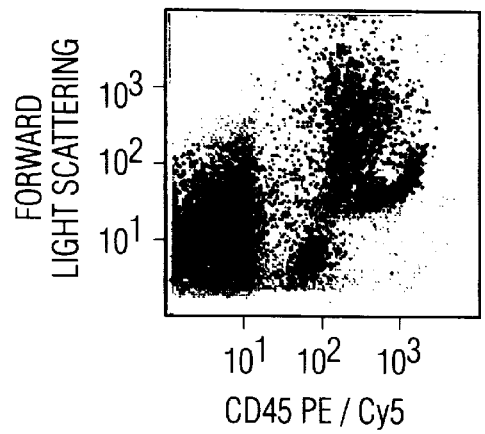

These Figures are to be compared with the FIGS. 1–4 of U.S. Pat. No. 5,047,321. As can be seen, the present invention provides additional information and detail not present in U.S. Pat. No. 5,047,321.

To increase the discrimination within the immature cells of the erythroid lineage and leukocytes, a threshold (or "gate") was applied on TO staining. This eliminated the mature erythrocytes. To further increase the resolution of cells within the leukocyte population, the light scattering amplifiers on the flow cytometer were run on linear (instead of the usual logarithmic) and the orthogonal light scatter data was transformed as described in U.S. Pat. No. 5,224,058.

Referring to FIG. 3, six dot plots are shown using the TO threshold and orthogonal light transformation for the peripheral blood sample in FIG. 1; however, in FIG. 3, platelets and mature reticulocytes as depicted as gray, immature reticulocytes are depicted as dark blue, neutrophils as green, lymphocytes as red and monocytes as light blue. In FIG. 4, six dot plots are shown for the fetal bone marrow sample of FIG. 2 using the TO and orthogonal light scatter transformation of FIG. 3. In FIG. 4, the color scheme is the same as in FIG. 3, however, progenitor cells are depicted as yellow, stromal and epithelial cells as black and nucleated erythrocytes as violet.

Referring to FIGS. 3 and 4, two populations of reticulocytes are evident based upon the intensity of staining with CD71. The immature reticulocytes (dark blue) and mature reticulocytes (gray) show differential expression of CD71. This permits a further division among the erythrocyte precursors. In addition, nucleated erythrocytes (violet) can be separated from the immature reticulocytes (dark blue) based upon more intense staining with TO and separated from leukocytes and stromal and epithelial cells based upon the absence of CD45 and CD71 fluorescence. Within the nucleated erythrocytes (violet), two cell populations can be identified. Immature cells dimly express CD45 while mature cell do not express CD45.

Referring to FIG. 4, the positions of non-hematopoietic cells are shown. These cells are depicted as black. These black colored cells show high intensity of expression with TO (i.e., they are nucleated) but lack expression of CD71 and dimly express CD45. The varied light scattering parameters for these cells is indicative of their heterogeneity (i.e., the cells include fibroblasts, endothelial cells and osteoclasts as determined by microscopic examination).

All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed is:

1. A method for the multi-parameter analysis of cells in a body fluid wherein said method comprises the steps of:
   1) taking a fluid sample from an individual;
   2) adding to said sample a nucleic acid dye;
   3) adding to said sample a first fluorescently labelled monoclonal antibody and a second fluorescently labelled monoclonal antibody, wherein said first antibody recognizes an antigen that is differentially expressed on said cells and wherein said second antibody recognizes an antigen that is differentially expressed on erthrocyte precursors and proliferating cells, and further wherein the fluorescent labels on said antibodies have peak emission spectra different from each other and from said nucleic acid dye;
   4) analyzing said cells in an instrument capable of detecting and recording at least three channels of fluorescence and at least two channels of light scatter for each of the cells in said sample, wherein erythrocytes, mature reticulocytes, immature reticulocytes, mature nucleated erythrocytes, immature nucleated etyhrocytes, progenitors, megakazyocytes, neutrophils, eosinophils, basophils, monocytes, lymphocytes, stromal and epithelial cells are identified, characterized and enumerated.

2. The method of claim 1 wherein the body fluid comprises peripheral blood.

3. The method of claim 1 wherein the body fluid comprises bone marrow.

4. The method of claim 1 wherein the nucleic acid dye is Thiazole Orange.

5. The method of claim 1 wherein the first monoclonal antibody is an anti-CD45 monoclonal antibody.

6. The method of claim 1 wherein the second monoclonal antibody is an anti-CD71 monoclonal antibody.

7. The method of claim 1 wherein steps 2) and 3) are combined.

8. The method of claim 1 wherein a third fluorescently labelled monoclonal antibody is added wherein said antibody recognizes antigens differentially expressed on platelets.

9. The method of claim 8 wherein said third monoclonal antibody is selected from the group consisting of an anti-CD61, anti-CD41 or anti-CD42 and pan-platelet monoclonal antibody.

10. The method of claim 1 wherein said labels are selected from the group consisting of phycoerythrin, fluorescein isothiocyanate, allophycocyanin, Texas Red, CY5, peridinin chlorophyll complex and phycoerythrin conjugates thereof.

11. The method of claim 1 wherein the monoclonal antibodies are conjugated directly to said labels.

12. A method for the multi-parameter analysis of cells in a body fluid wherein said method comprises the steps of:
   1) taking a sample of peripheral blood from an individual;
   2) adding to said sample Thiazole Orange;
   3) adding to said sample a fluorescently labelled anti-CD45 monoclonal antibody and a fluorescently labelled anti-CD71 monoclonal antibody, wherein the fluorescent labels on said antibodies have peak emission spectra different from each other and from Thiazole Orange;
   4) analyzing said cells in a flow cytometer capable of detecting and recording at least three channels of fluorescence and at least two channels of light scatter for each of the cells in said sample, wherein erythrocytes, mature reticulocytes, immature reticulocytes, mature nucleated exythrocytes, immature nucleated ethrocytes, progenitors, megakaryocytes, neutrophils, eosinophils, basophils, monocytes, lymphocytes, stromal and epithelial cells are identified, characterized, and enumerated.

13. The method of claim 12 wherein said labels are selected from the group consisting of phycoerythrin, fluorescein isothiocyanate, allophycocyanin, Texas Red, CY5, peridinin chlorophyll complex and phycoerythrin conjugates thereof.

14. A method for the multi-parameter analysis of cells in a body fluid wherein said method comprises the steps of:
   1) taking a sample of bone marrow from an individual;
   2) adding to said sample Thiazole Orange;
   3) adding to said sample a fluorescently labelled anti-CD45 monoclonal antibody and a fluorescently labelled anti-CD71 monoclonal antibody, wherein the fluorescent labels on said antibodies have peak emission spectra different from each other and from Thiazole Orange;
   4) analyzing said cells in a flow cytometer capable of detecting and recording at least three channels of fluorescence and at least two channels of light scatter for each of the cells in said sample, wherein erythrocytes, mature reticulocytes, immature reticulocytes, mature nucleated erythrocytes, immature nucleated erythrocytes, progenitors, megakaryocytes, neutrophils, eosinophils, basophils, monocytes, lymphocytes, stromal and epithelial cells are identified, characterized, and enumerated.

15. The method of claim 14 wherein said labels are selected from the group consisting of phycoerythrin, fluorescein isothiocyanate, allophycocyanin, Texas Red, CY5, peridinin chlorophyll complex and phycoerythrin conjugates thereof.

* * * * *